(12) United States Patent
Chung (10) Patent No.: US 10,828,628 B2
(45) Date of Patent: *Nov. 10, 2020

(54) HOMOGENEOUS CATALYSTS THAT ARE RECOVERABLE BY HOST-GUEST INTERACTIONS

(71) Applicant: Florida State University Research Foundation, Inc., Tallahassee, FL (US)

(72) Inventor: Hoyong Chung, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/433,929

(22) Filed: Jun. 6, 2019

(65) Prior Publication Data

US 2019/0344255 A1 Nov. 14, 2019

Related U.S. Application Data

(62) Division of application No. 15/682,991, filed on Aug. 22, 2017, now Pat. No. 10,357,763.

(60) Provisional application No. 62/377,777, filed on Aug. 22, 2016.

(51) Int. Cl.

| | | |
|---|---|---|
| *C07C 209/68* | (2006.01) | |
| *C07C 67/333* | (2006.01) | |
| *C07C 41/30* | (2006.01) | |
| *C07C 41/28* | (2006.01) | |
| *C07C 29/56* | (2006.01) | |
| *C07C 29/46* | (2006.01) | |
| *C07D 307/28* | (2006.01) | |
| *C07D 223/10* | (2006.01) | |
| *C07D 211/70* | (2006.01) | |
| *C07D 211/02* | (2006.01) | |
| *C07D 209/70* | (2006.01) | |
| *C07D 209/48* | (2006.01) | |
| *B01J 38/52* | (2006.01) | |
| *B01J 35/12* | (2006.01) | |
| *B01J 31/40* | (2006.01) | |
| *B01J 31/22* | (2006.01) | |
| *B01J 31/12* | (2006.01) | |
| *C07H 3/06* | (2006.01) | |
| *C08B 37/16* | (2006.01) | |
| *C07C 209/70* | (2006.01) | |
| *C07D 207/20* | (2006.01) | |
| *C07F 15/00* | (2006.01) | |
| *C08F 132/08* | (2006.01) | |

(52) U.S. Cl.
CPC ......... *B01J 31/2278* (2013.01); *B01J 31/123* (2013.01); *B01J 31/2208* (2013.01); *B01J 31/2273* (2013.01); *B01J 31/4023* (2013.01); *B01J 31/4038* (2013.01); *B01J 35/12* (2013.01); *B01J 38/52* (2013.01); *C07C 29/46* (2013.01); *C07C 29/56* (2013.01); *C07C 41/28* (2013.01); *C07C 41/30* (2013.01); *C07C 67/333* (2013.01); *C07C 209/68* (2013.01); *C07C 209/70* (2013.01); *C07D 207/20* (2013.01); *C07D 209/48* (2013.01); *C07D 211/02* (2013.01); *C07D 211/70* (2013.01); *C07D 223/10* (2013.01); *C07D 307/28* (2013.01); *C07F 15/0046* (2013.01); *C07H 3/06* (2013.01); *C08B 37/0012* (2013.01); *C08B 37/0015* (2013.01); *C08F 132/08* (2013.01); *B01J 2231/543* (2013.01); *B01J 2531/821* (2013.01); *B01J 2540/10* (2013.01); *B01J 2540/64* (2013.01); *C07C 2601/10* (2017.05); *C07C 2603/74* (2017.05); *Y02P 20/584* (2015.11)

(58) Field of Classification Search
CPC .............. B01J 31/2278; C08B 37/0015; C08B 37/0012; C07C 67/333; C07C 29/56; C07C 29/46; C07C 41/30; C07C 41/28; C07H 3/06
See application file for complete search history.

(56) References Cited

U.S. PATENT DOCUMENTS 4,792,620 A * 12/1988 Paulik .................. B01J 31/0231
560/232

OTHER PUBLICATIONS

Norskov et al, Nature Chemistry, Towards the Computational Design of Solid Catalysts, 2009, 1, pp. 37-46. (Year: 2009).*
Cullen et al, Chemical Science, Virtual screening for high affinity guests for synthetic supramolecular receptors, 2015, 6, pp. 2790-2794. (Year: 2015).*
Voskuhl et al, Chemical Communications, Optical Control Over Bioactive Ligands at Supramolecular Surfaces, 2014, 50, pp. 15144-15147. (Year: 2014).*
Skowerski et al.; "Exceptionally Stable and Efficient Solid Supported Hoveyda-Type Catalyst"; American Chemical Society, Organic Process Research and Development; vol. 19, pp. 872-877; 2015.
Skowerski et al.; "Highly Active Catalysts for Olefin Metathesis in Water"; The Royal Society of Chemistry, Catal. Sci. Technol.; vol. 2; pp. 2424-2427; 2012.
Skowerski et al.; "Ru-Based Complexes with Quaternary Ammonium Tags Immobilized on Mesoporous Silica as Olefin Metathesis Catalysts"; American Chemical Society; ACS Catalysis; vol. 4, pp. 3227-3236; 2014.
Smithson et al.; The Effect of Azobenzene Derivatives on UV-Responsive Organic Thin-Film Transistors with a 2,7-Dipentylbenzo[b] benzo[4,5] thieno-[2,3-d] thiophene Semiconductor; Royal Society of Chemistry, J. Mater. Chem C., vol. 3; pp. 8090-8096; 2015.

(Continued)

*Primary Examiner* — Paul A Zucker
(74) *Attorney, Agent, or Firm* — Christopher M. Ramsey; GrayRobinson, P.A.

(57) ABSTRACT

A method for separating a homogeneous catalyst from a solution includes forming a host-guest compound between a first isomer of the catalyst and inclusion compound in the solution and isolating the host-guest compound from the solution. The catalyst may be released from the inclusion compound by converting the first isomer of the catalyst to a second isomer of the catalyst.

12 Claims, 6 Drawing Sheets

(56) References Cited

OTHER PUBLICATIONS

Snelders et al.; "Steric,, Electronic, and Secondary Effects on the Coordination Chemistry of Ionic Phosphine Ligands and the Catalytic Behavior of their Metal Complexes"; Chemistry European Journal; vol. 17, pp. 42-57; 2011.
Song et al.; "Cyclic Alternating Ring-Opening Metathesis Polymerization (CAROMP) Rapid Access to Functionalized Cyclic Polymers"; Organic Letters; vol. 12, pp. 3729-3731; 2010.
Suriboot et al.; "Polyethylene as a Cosolvent and Catalyst Support in Ring-Opening Metathesis Polymerization"; American Chemical Society, Macromolecules; vol. 48,, pp. 5511-5516; 2015.
Suriboot et al.; "Supported Catalysts Useful in Ring-Closing Metathesis, Cross Metathesis, and Ring-Opening Metathesis Polymerization"; Polymers, vol. 8, No. 140; pp. 1-23; 2016; www.mdpi.com/journal/polymers.
Szczepaniak et al.; "Towards "Cleaner" Olefin Metathesis: Tailoring the NHC Ligand of Second Generation Ruthenium Catalysts to Afford Auxiliary Traits"; Royal Society of Chemistry, Green Chem., vol. 16; pp. 4474-4492; 2014.
Szente et al.; "Cyclodextrins in Analytical Chemistry: Host-Guest Type Molecular Recognition"; American Chemical Society; Anal. Chem.; vol. 85, pp. 8024-8030; 2013.
Tomasek et al.; "Olefin Metathesis in Aqueous Media"; Green Chem., vol. 15; pp. 2317-2338; 2013.
Tracz et al.; "Ammonium NHC-Tagged Olefin Metathesis Catalysts-Influence of Counter-Ions on Catalytic Activity"; Royal Society of Chemistry, New J. Chem., vol. 42; pp. 8609-8614; 2018.
Ulman et al.; "Ruthenium Carbene-Based Olefin Metathesis Initiators: Catalyst Decomposition and Longevity"; J. Org. Chem.; vol. 64, pp. 7102-7207: 1999.
Vapaavuori et al.; "Submolecular Plasticiztion Induced by Photons in Azobenzene Materials"; American Chemical Society, vol. 137, pp. 13510-13517; 2015.
Voskuhl et al: "Optical Control Over Bioactive Ligands at Supramolecular Srufaces"; Royal Society of Chemistry, Chem. Commun., vol. 50; pp. 15144-15147; 2014.
Vougioukalakis et al.; "Ruthenium-Based Heterocyclic Carbene-Coordinated Olefin Metathesis Catalysts"; Chem. Rev.,; vol. 110, pp. 1746-1787; 2010.
Vougioukalakis, Georgios C.; "Removing Ruthenium Residues from Olefin Metathesis Reaction Products"; Chem. Eur. Journal; vol. 18, pp. 8868-8880; 2012.
Wang et al.; "A Simple and Practical Preparation of an Efficient Water Soluble Olefin Metathesis Catalyst"; Royal Society of Chemistry, Green Chem., vol. 17; pp. 3407-3414; 2015.
Westhus et al.; "An Efficient and Inexpensive Scavenger Resin for Grubbs' Catalyst"; Tetrahedron Letters; vol. 45, pp. 3141-3142; 2004.
Yoshida et al.; "Tag Strategy for Separation and Recovery"; Chem. Rev.; vol. 102, pp. 3693-3716; 2002.
Zalipsky; "Chemistry of Polyethylene Glycol Conjugates With Biologically Active Molecules"; Advanced Drug Delivery Reviews; vol. 16, pp. 157-182; 1995.
Zhang et al.; "A Thermoresponsive Hydrogel Formed from a Star-Star Supramolecular Architecture"; Angew. Chem. Int. Ed.; vol. 52, pp. 6180-6184; 2013.
Zhang et al.; "Click Synthesis of a Novel Triazole Bridged AIE Active Cyclodextrin Probe for Specific Detection of Cd2+"; Royal Society of Chemistry, Chem. Commun. vol. 51; pp. 4298-4301; 2015.
Zhou et al.; "Photoinduced Triple Shape Memory Polyurethane Enabled by Doping With Azobenzene and GO"; Royal Society of Chemistry, J. Mater. Chem. C., vol. 4; pp. 9993-9997; 2016.
Zhu et al.; "Photoswitchable Supramolecular Catalysis by Interparticle Host-Guest Competitive Binding"; Chemistry a European Journal; vol. 18, pp. 13979-13983; 2012.

Ackermann et al; "Ruthenium Carbene Complexes with Imidazolin-2-ylidene Ligands Allow the Formation of Tetrasubstituted Cycloalkenes by RCM"; Tetrahedron Letters; vol. 40, pp. 4787-4790; 1999.
Ahn et al.; "A Convenient Method for the Efficient Removal of Ruthenium Byproducts Generated During Olefin Metathesis Reactions"; Organic Letters; vol. 3, pp. 1411-1413; 2001.
Allen et al.; "Well-Defined Silica-Supported Olefin Metathesis Catalysts"; Organic Letters, vol. 11, pp. 1261-1264; 2009.
Arduengo et al.; "A Stable Crystalline Carbene"; American Chemical Society, vol. 113, Pgds. 361-363; 1991.
Barbaro et al.; "Ion Exchange Resins: Catalyst Recovery and Recycle"; Chem. Rev.; vol. 109, pp. 515-529: 2009.
Behr et al.; "Thermoregulated Liquid/Liquid Catalyst Separation and Recycling"; Adv. Synth. Catal; vol. 348; pp. 1485-1495; 2006.
Bergbreiter, David E.; "Using Soluble Polymers to Recover Catalysts and Ligands"; Chem. Review, vol. 102; pp. 3345-3384; 2002.
Blass et al.; "Switching Adhesion and Friction by Light Using Photosensitive Quest-Host Interactions"; Royal Society of Chemistry, Chem. Commun., vol. 51; pp. 1830-1833; 2015.
Blencowe et al.; Ring-Opening Metathesis Polymerization with the Second Generation Hoveyda-Grubbs Catalyst: An Efficient Approach Toward High-Purity Functionalized Macrocyclic Oligo (cyclooctene)s; J. Am. Chem. Soc., vol. 135, pp. 5717-5725; 2013.
Buchmeiser, Michael R.; "Polymer Supported Well Defined Metathesis Catalysts"; Chem Rev., vol. 109, pp. 303-321; 2009.
Bucko et al.; "Synthesis of Organic-Inorganic Hybrid Azobenzene Materials for the Preparation of Nanofibers by Electrospinning"; Optical Materials, vol. 38, pp. 179-187; 2014.
Burtscher et al.; "Aqueous Olefin Metathesis"; Angew Chem. Int. Ed.; vol. 48; pp. 442-454; 2009.
Chapman; "PEGylated Antibodies and Antibody Fragments for Improved Therapy: a Review"; Advanced Drug Delivery Reviews; vol. 54, pp. 531-545; 2002.
Chatterjee et al.; "A General Model for Selectivity in Olefin Cross Metathesis"; American Chemical Society, vol. 125, pp. 11360-11370; 2003.
Chen et al.; "Polyethylene Glycol and Solutions of Polyethylene Glycol as Green Reaction Media"; The Royal Society of Chemistry; Green Chem; vol. 7; pp. 64-82; 2005.
Chen et al.; Supported Ruthenium-Carbene Catalyst on Lonic Magnetic Nanoparticles for Olefin Metathesis; American Chemical Society; Organic Letters, vol. 16, pp. 4969-4971; 2014.
Chen et al.; "The effect of Silica-Coating on Catalyst Recyclability in Ionic Magnetic Nanoparticle-Supported Grubbs-Hoveyda Catalysts for Ring-Closing Metathesis"; Tetrahedron; vol. 71, pp. 648-653; 2015.
Chen et al; "Cyclodextrin-Based Inclusion Complexation Bridging Supramolecular Chemistry and Macromolecurar Sel-Assembly"; The Royal Society of Chemistry; Chem. Soc. Rev.; vol. 40; pp. 2254-2266; 2011.
Cheng et al.; "Electrically Switchable and Permanently Stable Light Scattering Modes by Dynamic Fingerprint Chiral Textures"; Applied Materials and Interfaces; vol. 8; pp. 10483-10493; 2016.
Cho et al.; "An Efficient Method for Removal of Ruthenium Byproducts from Olefin Metathesis Reactions"; Organic Letters; vol. 5, pp. 531-533; 2003.
Clavier et al.; "Sustainable Concepts in Olefin Metathesis"; Angew Chem., Int. Ed., vol. 46; pp. 6786-6801; 2007.
Coperet et al.; "Strategies to Immobilize Well-Defined Olefin Metathesis Catalysts: Supported Homogeneous Catalysis vs. Surface Organometallic Chemistry"; Chem. Review; Adv. Synth. Catal.; vol. 349, pp. 78-92; 2007.
Courchay et al.; "Understanding Structural Isomerization During Ruthenium-Catalyzed Olefin Metathesis: A Deuterium Labeling Study"; American Chemical Society, Organometallics; vol. 25, pp. 6074-6068; 2006.
Crini, Gregorio; "Review: A History of Cyclodextrins"; Chem. Rev.; vol. 114, pp. 10940-10975; 2014.
Cullen et al.; "Virtual Screening for High Affinity Guests for Synthetic Supramolecular Receptors"; vol. 6, pp. 2790-2794; 2015.
Deshmukh et al.; "Alkene Metathesis: The Search for Better Catalysts"; The Royal Society of Chemistry; J. Mater Chem.; vol. 17; pp. 4249-4254; 2007.

(56) References Cited

OTHER PUBLICATIONS

Doppiu et al.; "Synthesis Optimization and Catalytic Activity Screening of Industrially Relevant Ruthenium-Based Metathesis Catalysts"; Top Catal, vol. 57, pp. 1351-1358; 2014.

Engel et al.; Loss and Reformation of Ruthenium Alkylidene: Connecting Olefin Metathesis, Catalyst Deactivation, Regeneration, and Isomerization; J. Am. Chem. Soc., vol. 139, pp. 16609-16619; 2017.

Galan et al.; "A Rapid and Simple Cleanup Procedure for Metathesis Reactions"; Organic Letters; vol. 9, pp. 1203-1206; 2007.

Gallivan et al.; "A Neutral, Water-Soluble Olefin Metathesis Catalyst Based on an N-Heterocyclic Carbene Ligand"; Tetrahedron Letters; vol. 46, pp. 2577-2580; 2005.

Gallou et al.; "A Practical Method for the Removal of Ruthenium Byproducts by Supercritical Fluid Extraction"; American Chemical Society, Organic Research and Development; vol. 10, No. 5; pp. 937-940; 2006.

Garber et al.; "Efficient and Recyclable Monomeric and Dendritic Ru-Based Metathesis Catalysts"; J. Am. Chem. Soc.; vol. 122, pp. 8168-8179; 2000.

Gessler et al.; "Synthesis and Metathesis Reactions of a Phosphine-Free Dihydroimidazole Carbene Ruthenium Complex"; Tetrahedron Letters; vol. 41, pp. 9973-9976; 2000.

Groot, R., ; "Mechanochemical Activation of Latent N-Heterocyclic Carbene Catalysts"; Techische Univeriteit, Eiddhoven, University of Technology; Jan. 1, 2013.

Gulajski et al; "A Highly Active Aqueous Olefin Metathesis Catalyst Bearing a Quaternary Ammonium Group"; ChemSusChem; vol. 1, pp. 103-109; 2008.

Harada et al.; "Supramolecular Polymeric Materials Via Cyclodextrin-Guest Interactions"; American Chemical Society; vol. 47; pp. 2128-21401; 2014.

Heppekausen et al.; "Rendering Schrock-Type Molybdenum Alkylidene Complexes Air Stable: User-Friendly Precatalysts for Alkene Metathesis"; Angew Chem., Int. Ed.; vol. 50, pp. 7829-7832; 2011.

Herbert et al.; "Z-Selective Cross Metathesis with Ruthenium Catalysts: Synthetic Applications and Mechanistic Implications"; Angew Chem. Int. Ed.; vol. 54, pp. 5018-5024; 2015.

Herrmann et al.; "Water-Soluble Ligands, Metal Complexes, and Catalysts: Synergism of Homogeneous and Heterogeneous Catalysis"; Agnew. Chem. Int. Ed. vol. 32, pp. 1524-1544; 1993.

Hobbs et al.; "Thermomorphic Polyethylene-Supported Olefin Metathesis Catalysts"; Organic Letters; vol. 13, pp. 3904-3907; 2011.

Hong et al.; "Decomposition of a Key Intermediate in Rutheniumm Catalyzed Olefin Metathesis Reactions"; American Chemical Society, vol. 126, pp. 7414-7415; 2004.

Hong et al.; "Efficient Removal of Ruthenium Byproducts from Olefin Metathesis Products by Simple Aqueous Extraction"; Organic Letters; vol. 9, pp. 1955-1957; 2007.

Hong et al.; "Highly Active Water-Soluble Olefin Metathesis Catalyst"; American Chemical Society, vol. 128, pp. 3508-3509; 2006.

Hong et al.; "Prevention of Undesirable Isomerization During Olefin Metathesis"; American Chemical Society, vol. 127, pp. 17160-17161; 2005.

Hongfa et al.; "Heptane-Soluble Ring-Closing Metathesis Catalysts"; Organic Letters; vol. 9, pp. 3259-3261; 2007.

Hongfa et al.; "Polyisobutylene-Anchored N-Heterocyclic Carbene Ligands"; Organic Letters; vol. 11, pp. 665-667; 2009.

Huang et al.; "Olefin Metathesis-Active Ruthenium Complexes Bearing a Nucleophilic Carbene Ligand"; J. Am. Chem. Soc., vol. 121, pp. 2674-2678; 1999.

Isenbugel et al.; "Photo-Switchable Behavior of Azobenzene-Dye-Modified Silica Nanoparticles and Their Assembly with Cyclodextrin Derivatives"; Marcomolecular Chemistry and Physics, vol. 213, pp. 227-233: 2012.

Joo et al.; "Recent Developments in Aqueous Organometallic Chemistry and Catalysis"; Journal of Molecular Catalysis A: Chemical; vol. 116, pp. 3-26; 1997.

Jordan et al.; "Small-Molecule N-Heterocyclic-Carbene-Containing Olefin-Metathesis Catalysts for Use in Water"; Angew. Chem., vol. 119, pp. 5244-5247; 2007.

Khan et al.; "Methods for Selective Modifications of Cyclodextrins"; Chem. Rev.; vol. 98, pp. 1977-1996; 1998.

Kim et al.; "Removable Water-Soluble Olefin Metathesis Catalyst Via Host-Guest Interaction"; Organic Letters; vol. 20, pp. 736-739; 2018.

Kingsbury et al.; "A Recyclable Ru-Based Metathesis Catalyst"; J. Am. Chem. Soc., vol. 121. pp. 791-799; 1999.

Kingsbury et al.; "Immobilization of Olefin Metathesis Catalysts on Monolithic Sol-Gel: Practical, Efficient, and Easily Recyclable Catalysts for Organic and Combinatorial Synthesis"; Angew. Chem. Int. Ed.; vol. 40, No. 22; pp. 4251-4256; 2001.

Klucir et al.; "Ruthenium-Based Complexes Containing a Benzimidazolium Tag Covalently Connected to N-Heterocyclic Carbene Ligands: Environmentally Friendly Catalysts for Olefin Metathesis Transformations"; The Royal Society of Chemistry; Dalton Trans.; vol. 42; pp. 7354-7358; 2013.

Kosnik et al.; "Synthesis of Functionalised N-Heterocyclic Carbene Ligands Bearing a Long Spacer and Their Use in Olefin Metathesis"; Dalton Transactions; vol. 42; pp. 7463-7467; 2013.

Krisfina et al.; "Light-Responsive Molecular Recognition and Adhesion of Vesicles"; Angew. Chem. Int. Ed.; vol. 49, pp. 5371-5374; 2010.

Lee et al.; "New Azobenzene Non-Linear Optical Materials for Eye and Sensor Protection"; Optical Materials; vol. 32, pp. 147-153; 2009.

Lehn, Jean-Marie; "Towards Complex Matter: Supramolecular Chemistry and Self-organization"; European Review, vol. 17, No. 2; pp. 263-280; 2009.

Li et al.; "A Highly Active and Reusable Heterogeneous Ruthenium Catalyst for Olefin Metathesis"; Adv. Synth. Catal., vol. 347, pp. 1745-1749; 2005.

Li et al.; "Cyclodextrin-Based Supramolecular Architectures: Syntheses, Structures, and Applications for Drug and Gene Delivery"; Advanced Drug Delivery Reviews; vol. 60, pp. 1000-1017; 2008.

Liao et al.; "Photoresponsive Pseudopolyrotaxane Hydrogels Based on Competition of Host-Guest Interactions"; Angew Chem. vol. 122, pp. 4511-4515; 2010.

Liu et al.; "Reversible Aggregation of Gold Nanoparticles Driven by Inclusion Complexation"; The Royal Society of Chemistry; J. Mater Chem.; vol. 17; pp. 4249-4254; 2007.

Ma et al.; "Biomedical Applications of Supramolecular Systems Based on Host Guest Interactions"; American Chemical Society, Chem. Rev.; vol. 115, pp. 7794-7839; 2015.

Marcet et al.; "Sol-Gel Immobilized Hoveyda-Grubbs Complex Through the NHC Ligand: A Recyclable Metathesis Catalyst"; Journal of Molecular Catalysis A: Chemical; vol. 357, pp. 59-66; 2012.

Maynard et al.; "Purification Technique for the Removal of Ruthenium from Olefin Metathesis Reaction Products"; Tetrahedron Letters; vol. 40, pp. 4137-4140; 1999.

Mayr et al.; "Monolithic Disk-Supported Metathesis Catalysts for Use in Combinatorial Chemistry"; Adv. Synth. Catal.; vol. 347, pp. 484-492; 2005.

Mayr et al.; "Monolithic Materials: New High-Performance Supports for Permanently Immobilized Metathesis Catalysts"; Angew. Chem. Int. Ed.; vol. 40, pp. 3839-3842; 2001.

Mayr et al.; "Synthesis of a Silica-Based Heterogeneous Second Generation Grubbs Catalyst"; Adv. Synth. Catal.; vol. 344, pp. 712-719; 2002.

McEleney et al.; "Functionalized Mesoporous Silicates for the Removal of Ruthenium from Reaction Mixtures"; Organic Letters; vol. 8, pp. 2663-2666; 2006.

Michrowska et al.; "A Green Catalyst for Green Chemistry; Synthesis and Application of an Olefin Metathesis Catalyst Bearing a Quaternary Ammonium Group"; The Royal Society of Chemistry; Green Chem.; vol. 8; pp. 685-688; 2006.

Mohr et al.; "Synthesis of Water-Soluble, Aliphatic Phosphines and Their Application to Well-Defined Ruthenium Olefin Metathesis Catalysts"; American Chemical Society, Organometallics; vol. 15, No. 20; pp. 4317-4325; 1996.

(56) References Cited

OTHER PUBLICATIONS

Muderawan et al.; "A Reliable Synthesis of 2-and 6-amino β-cyclodextrin"; Tetrahedron Letters; vol. 46, pp. 7905-7907; 2005.
Nelson et al.; "Key Processes in Ruthenium-Catalysed Olefin Metathesis"; Royal Society of Chemistry, Chem. Comm.; Vo. 50; pp. 10355-10375; 2014.
Nguyen et al.; "Ring Opening Metathesis Polymerizaton (ROMP) of Norbornene by a Group VIII Carbene Complex in Protic Media"; J. Am. Chem. Society; vol. 114, pp. 3974-3975; 1992.
Norskov et al.; "Nature Chemistry, Towards the Computational Design of Solid Catalysts"; vol. 1, pp. 37-46; 2009.
Office Action dated Jan. 3, 2019—U.S. Appl. No. 15/682,991.
Olszewski et al.; "A New Tool in the Toolbox; Electron-Withdrawing Group Activated Ruthenium Catalysts for Olefin Metathesis"; Synlett; vol. 24, pp. 903-919; 2013.
Ondrusek et al.; "Modified N-Heterocyclic Carbene Ligand for the Recovery of Olefin Metathesis Catalysts Via Noncovalent Host-Guest Interactions"; ACS Omega; vol. 2; pp. 3951-3957; 2017.
Paquette et al.; "A Convenient Method for Removing All Highly-Colored Byproducts Generated During Olefin Metathesis Reactions"; Organic Letters; vol. 2, pp. 1260-1261; 2000.
Pouliquen et al.; "Photoresponsive Viscosity and Host-Guest Association in Aqueous Mixtures of Poly-Cyclodexrin with Azobenzene-Modified Poly(Acrylic) Acid"; J. Phys. Chem. B., vol. 111, pp. 5587-5595; 2007.
Probst et al.; "Athermal Azobenzene-Based Nanoimprint Lithography"; Advanced Materials; vol. 28, pp. 2624-2628; 2016; www.advmat.de.
Qi et al.; "A Catch-Release Catalysis System Based on Supramolecular Host-Guest Interactions"; Royal Society of Chemistry, RSC Adv., vol. 6; pp. 23686-23692; 2016.
Raynal et al.; "Supramolecular Catalysis. Part 1: non-Covalent Interactions as a Tool for Building and Modifying Homogeneous Catalysts"; Royal Society of Chemistry; vol. 43; pp. 1660-1733; 2014.
Rekharsky et al.; "Complexation Thermodynamics of Cyclodextrins"; Chem. Rev.; vol. 98, pp. 1875-1917; 1998.
Roling et al.; "Layer-by-Layer Deposition of Vesicles Mediated by Supramolecular Interaction"; American Chemical Society, vol. 29. pp. 10174-10182; 2013.
Samanta et al.; "A Synthesis of PEG-and Phosphorylcholine_Substituted Pyridines to Afford Water-Soluble Ruthenium Benzylidene Metathesis Catalysts"; American Chemical Society, Macromolecules; vol. 41, pp. 530-532; 2008.
Samanta et al.; "Metal Ion, Light, and Redox Responsive Interaction of Vesicles by a Supramolecular Switch"; Chemistry European Journal; vol. 20, pp. 4966-4973; 2014.
Samojlowicz et al.; "Ruthenium-Based Olefin Metathesis Catalysts Bearing N-Heterocyclic Carbene Ligands"; Chem. Rev.; vol. 109, pp. 3708-3742; 2009.
Schmidt et al.; "Dynamic Macromolecular Material Design—The Versatility of Cyclodextrin-Based Host-Guest Chemistry"; Angew Chem. Int. Ed.; vol. 56, pp. 8350-8369; 2017.
Schmidt, Bernd; Catalysis at Interface of Ruthenium Carbene and Ruthenium Hydride Chemistry: Organometallic Aspects and Applications to Organic Synthesis; European Journal Organic Chemistry; pp. 1865-1880; 2004; www.eurjoc.org.
Scholl et al.; "Increased Ring Closing Metathesis Activity of Ruthenium-Based Olefin Metathesis Catalysts Coordinated with Imidazolin 2-ylidene Ligands"; Tetrahedron Letters; vol. 40,. pp. 2247-2250; 1999.
Scholl et al.; "Synthesis and Activity of a New Generation of Ruthenium-Based Olefin Metathesis Catalysts Coordinated with 1,3-Dimesityly-4,5-dihydroimidazol-2-ylidene Ligands"; Organic Letters; vol. 1, pp. 953-956; 1999.
Schwab et al.; "A Series of Well-Defined Metathesis Catalysts—Synthesis of [RuCl2(=CHR')(PR3)2] and Its Reactions"; Angew. Chem. Int. Ed.; vol. 34 No. 18, pp. 2039-2041;1995.
Schwab et al.; "Synthesis and Application of RuCl2(=CHR')(PR3)2: The Influence of the Alkylidene Moiety on Metathesis Activity"; J. Am. Chem. Soc., vol. 118, pp. 100-110: 1996.
Shaughnessy, Kevin H.; "Hydrophilic Ligands and Their Application in Aqueous-Phase Metal-Catalyzed Reactions"; Chem. Rev.; vol. 109, pp. 643-710; 2009.
Shetty et al.; "Can We Beat the Biotin-Avidin Pair": Cucurbit[7] Uril-Based Ultrahigh Affinity Host-Guest Complexes and Their Applications; Royal Society of Chemistry, Chem. Soc. Rev.; vol. 44; pp. 8747-8761; 2015.
Skowerski et al.; "Easily Removable Olefin Metathesis Catalysts"; Green Chem., vol. 14; pp. 3264-3268; 2012.
Skowerski et al.; "Effective Immobilisation of a Metathesis Catalyst Bearing an Ammonium-Tagged NHC Ligand on Various Solid Supports"; Beilstein Journal of Organic Chemistry; vol. 12; pp. 5-15; 2016.

\* cited by examiner

Table 1. Metathesis Substrate and Host–Guest Recovery Scope[a]

| Entry | Substrate | Product | Conv. (%)[b] | [Ru] (ppm)[c] |
|---|---|---|---|---|
| 1 | EtO₂C CO₂Et (19) | EtO₂C CO₂Et cyclopentene (20) | >95% | 136[d], 57[e], 420[f], 136[g], 365[d] |
| 2 | EtO₂C CO₂Et (21) | EtO₂C CO₂Et methylcyclopentene (22) | >95% | N/A |
| 3 | EtO₂C CO₂Et (23) | EtO₂C CO₂Et dimethylcyclopentene (24) | 12% | — |
| 4 | allyl ether (25) | dihydrofuran (26) | >95% | 752[d] |
| 5 | Ts-N diallyl (27) | Ts-N cyclopentene (28) | >95% | 287[d] |
| 6 | Bz ketone (29) | Bn lactam (30) | >95% | 259[d] |
| 7 | AcO diallyl (31) | AcO / OAc (32) | >95% | 225[d] |
| 8 | Ph Ph propargyl (33) | Ph Ph dihydrofuran (34) | >95% | 52[d] |

[a]Reaction conditions: toluene (0.2 M) stirred for 30 min at 60 °C with 1 mol % catalyst 4. [b]Determined by ¹H NMR spectra analysis of crude reaction mixtures before catalyst recovery. [c]Determined by inductively coupled plasma mass spectrometry (ICP-MS) of crude reaction residues. [d]After treatment of reaction mixture twice with 2 equiv 18. [e]After treatment of reaction mixture six times with 2 equiv 18. [f]After treatment of reaction mixture once with 6 equiv 18. [g]After treatment twice with 2 equiv 18, stirring for 60 min instead of 15.

FIG. 8

HOMOGENEOUS CATALYSTS THAT ARE RECOVERABLE BY HOST-GUEST INTERACTIONS

CROSS-REFERENCE TO RELATED APPLICATION

This is a divisional of application Ser. No. 15/682,991, now U.S. Pat. No. 10,357,763, filed Aug. 22, 2017, which claims priority from provisional Application No. 62/377,777, filed Aug. 22, 2016, which are incorporated by reference in their entirety

FIELD

This relates to the field of catalysis and, more particularly, to recovery of homogeneous catalysts.

BACKGROUND

Homogeneous catalysts are used to catalyze many different chemical reactions and are invaluable tools in organic synthesis. But a major problem with homogeneous catalysts is that they are soluble in the reaction solution. Because they are soluble, they are difficult to recover from the solution after the reaction is completed. Much research has been devoted to recovering spent homogeneous catalysts, but the conventional catalysts and their associated recovery techniques have their drawbacks.

BRIEF SUMMARY

This disclosure describes homogeneous catalysts that are recoverable from solution by forming a host-guest compound in the solution. The host portion of the host-guest compound binds to the soluble catalyst, allowing the catalyst to be isolated from the solution.

An exemplary method for separating a homogeneous catalyst from a solution includes forming a host-guest compound between a first isomer of the catalyst and inclusion compound in the solution and isolating the host-guest compound from the solution. The catalyst may be released from the inclusion compound by converting the first isomer of the catalyst to a second isomer of the catalyst.

An exemplary method of performing a catalyzed chemical reaction includes catalyzing a chemical reaction in a solution using a homogeneous catalyst and adding an inclusion compound to the solution. The inclusion compound binds a first isomer of the catalyst to form a host-guest compound including the inclusion compound and first isomer of the catalyst. The host-guest compound is isolated from the solution and the catalyst is released from the inclusion compound by converting the first isomer of the catalyst to a second isomer of the catalyst.

These methods may include the following additional features.

The first isomer may be a cis or trans isomer and the second isomer is the other of a cis or trans isomer.

The catalyst may include a transition metal and an N-heterocyclic carbene moiety bonded to an azobenzene functional group.

The inclusion compound may be a cyclodextrin.

The inclusion compound may be a cyclodextrin attached to a surface of a substrate.

Converting the first isomer of the catalyst to a second isomer of the catalyst may include applying electromagnetic radiation.

The solution may be an olefin metathesis reaction solution.

An example of a homogeneous catalyst that may be used in the methods includes a transition metal complex having an N-heterocyclic carbene ligand with an azobenzene functional group thereon, the azobenzene functional group is effective to undergo cis-trans isomerization. The composition may also include a cyclodextrin moiety bound to the azobenzene functional group. A silica substrate may be attached to the cyclodextrin moiety.

DETAILED DESCRIPTION OF EXAMPLE EMBODIMENTS

A homogeneous catalyst is a catalyst that is in the same phase as the reactants. Thus, in a reaction solution the homogeneous catalyst is dissolved. In contrast, a heterogeneous catalyst is a catalyst that is in a different phase than the reactants. In a reaction solution, the heterogeneous catalyst is often a solid. This disclosure relates to homogeneous catalysts and their recovery from the reaction solution.

A host-guest compound is used in the catalyst recovery process. In general, a host-guest compound includes two or more molecules held together by non-covalent intermolecular forces. The host-guest compound includes an inclusion compound that acts as the host. The inclusion compound has a cavity that receives the catalyst (the guest). The catalyst is held within the cavity by intermolecular forces to form the host-guest compound.

In an example method employing this concept a homogeneous catalyst is separated from a solution by first forming a host-guest compound between a first isomer of the catalyst and inclusion compound in the solution. The host-guest compound is then isolated from the solution. The catalyst is subsequently released from the inclusion compound by converting the first isomer of the catalyst to a second isomer of the catalyst.

Certain organic functional groups undergo isomerization changes when external energy is applied. Examples of sources of external energy include, but are not limited to, electromagnetic radiation, heat, electricity, and the like.

For example, azobenzene moieties typically convert from the cis-isomer to the trans-isomer when visible electromagnetic radiation is applied and convert back to the cis-isomer when ultraviolet electromagnetic radiation is applied.

The method takes advantage of the fact that different isomers of a compound have different binding affinity for inclusion compounds. The trans-isomer of azobenzene, for example, forms a host-guest compound with Beta-cyclodextrin (BCD), whereas the cis-isomer does not. This different binding affinity permits the catalyst to bind to the inclusion compound for removal from solution, and then be released from the inclusion compound for reuse.

The process of forming the host-guest compound between the first isomer of the catalyst occurs in the solution. The kinetics of the formation reaction will vary based on the chemical nature of the inclusion compound and catalyst chosen. Accordingly, an external stimulus such as heat, stirring, ultrasound, or the like may increase the rate of formation of the host-guest compound. If necessary, external energy may be applied to the solution to ensure the catalyst is in its first isomer form.

Once formed, the host-guest compound may be insoluble in the solution, which causes it to precipitate. The precipitate may be separated from the solution using conventional solid-liquid separation technique such as filtration, centrifugation, or the like.

The catalyst may be released from the inclusion compound by converting the catalyst to a second isomer that does not have a binding affinity for the inclusion compound. When the catalyst converts to the second isomer, the intermolecular host-guest interaction diminishes and the catalyst and inclusion compound can be separated. The catalyst may be converted to the second isomer by applying external energy to the catalyst sufficient to cause the isomerization change.

The catalyst may be used to catalyze a chemical reaction, and then separated from the chemical reaction solution. In such a case, the catalyst is combined with the reactant(s) in the solution and the reaction is allowed to proceed. At the desired time after the reaction proceeds, the inclusion compound is added to the solution. The inclusion compound and catalyst form the host-guest compound. The host-guest compound is then isolated from the solution and the catalyst is released from the inclusion compound as discussed above.

The catalyst is particularly useful for catalyzing metathesis reactions, Suzuki-Miyaura Coupling, Buchwald-Hartwig Aminations, Negishi Reactions, Hiyama Coupling, Kumada Coupling, Sonogashira Coupling, Heck Reaction, Hydrosilylation, Allene Formation, 1,4-Reduction, Conjugate Addition, Hydrothiolation, Hydroalkoxylation, Hydroamination, Carboxylation & Carbonylation (via Boronic Acids and CH Activation), $CO_2$ Insertion, [3+2] Cycloaddition Reaction(Formation of Triazole), Allylic Substitution, other organo-catalytic reactions, among many others. Accordingly, the chemical reaction solution contains the reactant(s) associated with the reaction being catalyzed and, after the reaction proceeds, the chemical reaction solution will contain the reaction product(s).

The catalyst may be an organic or organometallic compound having an N-heterocyclic carbene moiety and an azobenzene moiety. The azobenzene moiety is capable of undergoing cis-trans isomerization in response to a stimulus having sufficient energy to cause the cis-trans isomerization.

The azobenzene moiety may be azobenzene itself or a functionalized azobenzene. A functionalized azobenzene includes an azobenzene backbone, but relative to azobenzene, the phenyl groups include one or more appended functional groups, such as, for example, alkanes, alkenes, alkynes, aldehydes, ketones, ethers, esters, alkoxys, and/or carboxylic acids.

The organometallic compound has a transition metal bonded to the N-heterocyclic carbene moiety and azobenzene moiety. The transition metal may be a transition metal that functions as a catalyst. Examples of such transition metals include Ru, Pd, Ni, Cu, Fe, Ag, Au, Rh, Ir, Ni, Pd, and Cu among others.

A particular example of the catalyst has the formula shown below.

Figure 1:
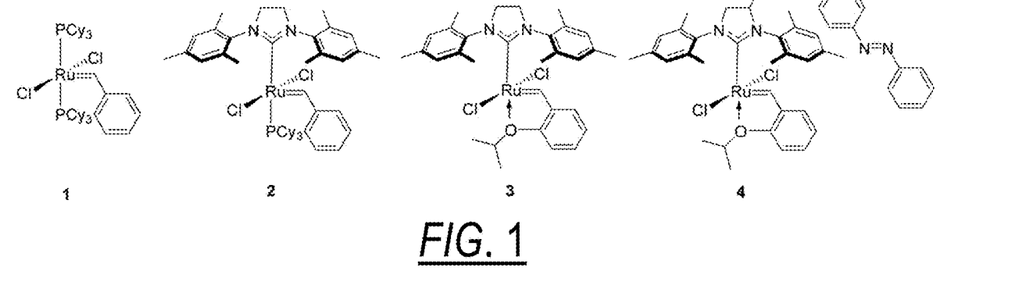
FIG. 1 depicts the chemical formula of a set of homogeneous catalysts.

In this formula, R represents the position of the azobenzene functional group. Compound 4 shown in FIG. 1 is an example of such a catalyst having this formula.

The inclusion compound may be any conventional inclusion compound used in host-guest chemistry, such as, for example, cyclodextrins, porphyrins, calixarenes, cucurbiturils, and crown ethers among others.

In certain examples a cyclodextrin is used as the inclusion compound and with catalyst having azobenzene-based functional groups. When the azobenzene-based functional groups are in the cis-isomer configuration, the catalyst does not interact with the inclusion compound sufficiently enough to hold the catalyst within the cavity. However, when the azobenzene-based functional groups are in the trans-isomer configuration, the inclusion compound holds the catalyst within the cavity, forming the host-guest compound. The external energy stimulus can be used to cause the azobenzene-based functional groups to convert between the cis- and trans-isomers, which modulates the catalyst's interaction with the cyclodextrin inclusion compound.

Cyclodextrins are oligosaccharides including a plurality of sugar molecules linked together to form a ring. Examples include, but are not limited to alpha-cyclodextrin, beta-cyclodextrin, and gamma-cyclodextrin. The cyclodextrin backbone may be functionalized as desired to modify its properties. For example, it may be modified with functional groups that modify the interaction with a particular catalyst.

The inclusion compound may be functionalized in such a way that it binds to a solid substrate surface such as a metal surface, a magnetic surface, a silica surface or the like. By attaching the inclusion compound to a surface, the inclusion compound becomes immobilized, which may make removing the inclusion compound from solution easier.

In a particular example, the substrate is silica such as activated silica. The surface of the silica may be functionalized with an isothiocyanate. The isothiocyanate portion acts as a bonding point for amines. Accordingly, if the inclusion compound is functionalized with a terminal amine group, it can be attached to the silica via the isothiocyanate group.

Silica is a porous material and may be used in particle form. Examples of sizes of silica particles include 50 to 300 mesh, 60 to 270 mesh, or 70 to 230 mesh. Examples of pore sizes include 10 to 200 Å, 30 to 150 Å, 20 to 80 Å, or about 60 Å.

EXAMPLE

This section discusses particular examples of the composition and methods for illustrative purposes. The scope of the claims is not limited to the details discussed in this section.
Synthesis of an Example of the Catalyst FIG. 1 displays four different olefin metathesis catalysts. Compounds 1, 2, and 3 are previously known. Compound 1 is called the Hoveyda-Grubbs first generation catalyst. Compound 2 is called the Hoveyda-Grubbs second generation catalyst. The synthesis of Compound 4 is discussed in this section.

Figure 2:
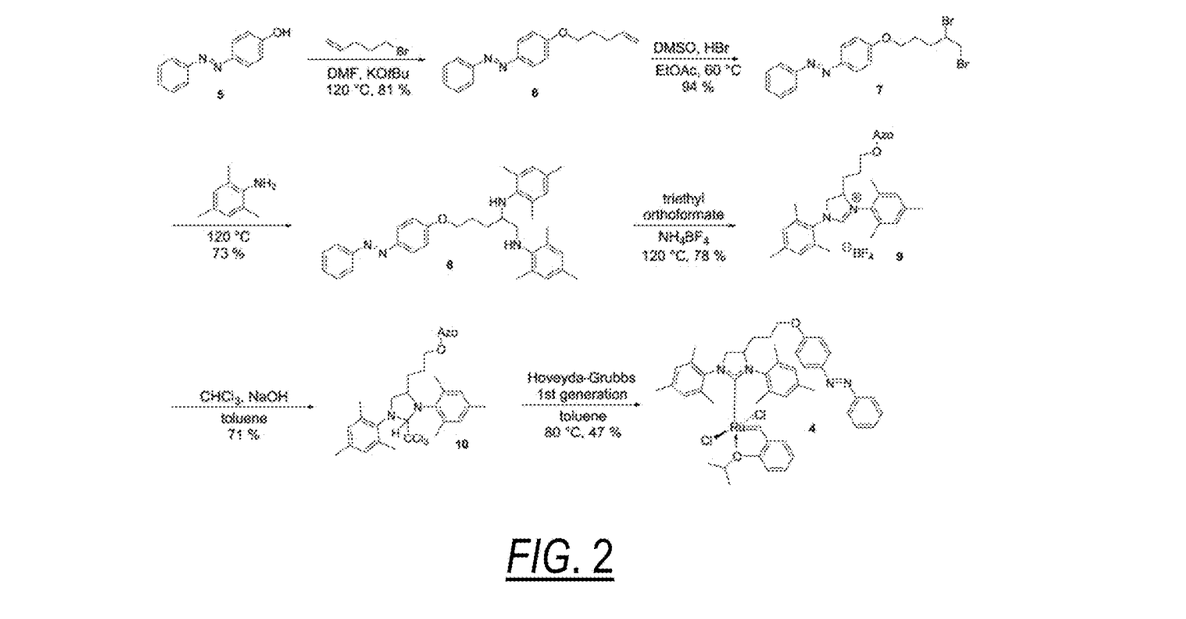
FIG. 2 is a reaction scheme illustrating an exemplary method of synthesizing Compound 4.

FIG. 2 outlines the method used to synthesize Compound 4. The method began with the alkylation of 4-phenylazophenol (Compound 5), followed by dibromination of the terminal alkene to produce dibromide (Compound 7), our biselectrophile intermediate.

Substitution under high-temperature conditions with 2,4,6-trimethylaniline, followed by workup, resulted in a diamine (Compound 8). The treatment of the resulting diamine with triethyl orthoformate and ammonium tetrafluoroborate resulted in the precipitation of the cyclized NHC precursor salt (Compound 9).

An indirect route toward the catalyst was ultimately successful involving the formation of an intermediate chloroform adduct (Compound 10) under basic conditions. Thermolysis of the chloroform adduct in the presence of the Hoveyda-Grubbs' first generation catalyst (Compound 1) resulted in the formation of Compound 4, which was isolated as a green/yellow band on a silica gel column.

Additional details of these steps follow.

Synthesis of Compound 6. A 100 mL round-bottom flask was charged with 4-phenylazophenol (2 g, 10.1 mmol, 1 equiv.) and potassium tert-butoxide (1.19 g, 10.6 mmol, 1.05 equiv.). These reagents were stirred together mechanically for 15 minutes prior to dissolution in anhydrous DMF (24 mL, 0.42 M). Once the solids had been dissolved, the reaction vessel was charged with 5-bromo-1-pentene (1.26 mL, 10.6 mmol, 1.05 equiv.) and the deep red reaction mixture was heated to 120° C. for 1 hour.

Upon completion of the reaction by TLC, the orange reaction mixture was diluted with water and extracted with hexanes several times. The combined organic layers were washed with water and brine, then dried over MgSO$_4$ and concentrated under reduced pressure. The resulting residue was adsorbed to silica gel and purified by column chromatography (100% hexanes to 9:1 hexanes:EtOAc) to yield 1.08 grams of the desired material as a bright orange solid. (4.05 mmol, 81% yield)

Synthesis of Compound 7. Compound 6 (1.5 g, 5.6 mmol, 1 equiv.) and DMSO (480 µL, 6.8 mmol, 1.2 equiv.) were charged to a 100 mL round-bottom flask and dissolved in ethyl acetate (23 mL, 0.25 M), with no special precautions taken toward air or moisture. Once heated to 60° C., the reaction vessel was charged with 48% aq. HBr (1.52 mL, 13.5 mmol, 2.4 equiv.) in one portion. The reaction was stirred at 60° C. for 30 minutes before being cooled to room temperature and concentrated under reduced pressure.

The resulting solid was redissolved in DCM and adsorbed to silica gel by gentle rotary evaporation, then purified by column chromatography (100% hexanes to 9:1 hexanes:EtOAc) to yield 2.17 grams of the desired product as a bright orange solid. (5.09 mmol, 94% yield).

Synthesis of Compound 8. A 100 mL round-bottom flask was charged with Compound 7 (9 g, 21.2 mmol, 1 equiv.) and freshly-distilled 2,4,6-trimethylanilne (30 mL, 211 mmol, 10 equiv.). The reaction vessel was fitted with a Vigreux column and stirred at 120° C. for 48 hours. The crude reaction mixture was then charged with 2 M NaOH (50 mL) and DCM (50 mL) and stirred for 30 minutes. The reaction was then extracted with DCM several times, and the combined organic layers were washed with water and brine, then dried over MgSO$_4$ and concentrated under reduced pressure.

The resulting black, tar-like material was vacuum distilled to remove excess 2,4,6-trimethylaniline (90° C. at 0.35 Torr) from the reaction mixture into the distillation flask. The crude product, without 2,4,6-trimethylaniline, was collected from the original flask and purified by column chromatography (20:1 to 9:1 Hexanes:EtOAc) to yield 8.6 grams of the desired material as a red oil. (16.1 mmol, 76% yield).

Synthesis of Compound 9. A 250 mL round-bottom flask was charged with Compound 8 (5.2 g, 9.7 mmol, 1 equiv.), ammonium tetrafluoroborate (1.22 g, 11.7 mmol, 1.2 equiv.) and triethyl orthoformate (54 mL, 0.18 M). The reaction vessel was fitted with a Vigreux column and placed in an oil bath so that only the very bottom of the flask came into contact with the oil (allowing for recrystallization of the product during formation). The reaction was then stirred with heating to 120° C. The formation of orange solid after 1 hour is indicative of a successful reaction, and the reaction mixture was stirred for a further 3 hours at 120° C.

After cooling to room temperature the reaction was diluted with an excess of diethyl ether and the heterogeneous slurry was vacuum filtered to give 4.39 grams of the desired product as an orange/yellow solid. (6.94 mmol, 78% yield).

Synthesis of Compound 10. A 250 mL Schlenk flask was charged with sodium hydroxide (2.53 g, 63.2 mmol, 40 equiv.) that had been ground to a fine powder via mortar and pestle immediately before addition. This was suspended in dry and degassed toluene (79 mL, 0.02 M) and stirred vigorously for 5 minutes before the reaction vessel was charged with dry chloroform (510 µL, 6.32 mmol, 4 equiv.). This suspension was stirred for 10 minutes before adding Compound 9 (1 g, 1.58 mmol, 1 equiv.) in one portion. The reaction was stirred vigorously at room temperature for 75 minutes.

The reaction was filtered to remove excess salts, and the orange solution was concentrated under reduced pressure to remove toluene. The resulting residue was purified by flash chromatography (9:1 Hexanes:EtOAc, dried prior to use) to yield 743 mg of the desired product as a yellow/orange solid after drying. (1.12 mmol, 71% yield) The product was found to be stable as a dry solid on the benchtop for several days.

Synthesis of Compound 4. A 25 mL Schlenk flask under light nitrogen flow was charged with NHC—CHCl$_3$ Compound 10 (442 mg, 0.67 mmol, 2 equiv.), Hoveyda-Grubbs 1$^{st}$ generation catalyst (200 mg, 0.299 mmol, 1 equiv.), and anhydrous toluene which had been degassed under nitrogen flow for 15 minutes (17 mL, 0.02M). This reaction mixture was heated with stirring to 80° C. for 75 minutes, after which time it was cooled to room temperature and the solvent was removed under reduced pressure.

The crude product was purified by silica gel chromatography, no special precautions were required regarding silica gel or solvent purity (9:1 to 7:3 hexanes:EtOAc, desired product appears as a dark green band following yellow and brown bands). The collected fractions were concentrated to yield 168 mg of the desired product as a dark yellow-green solid (0.194 mmol, 65% yield).

Synthesis of an Example of the Host Compound

Figure 3:
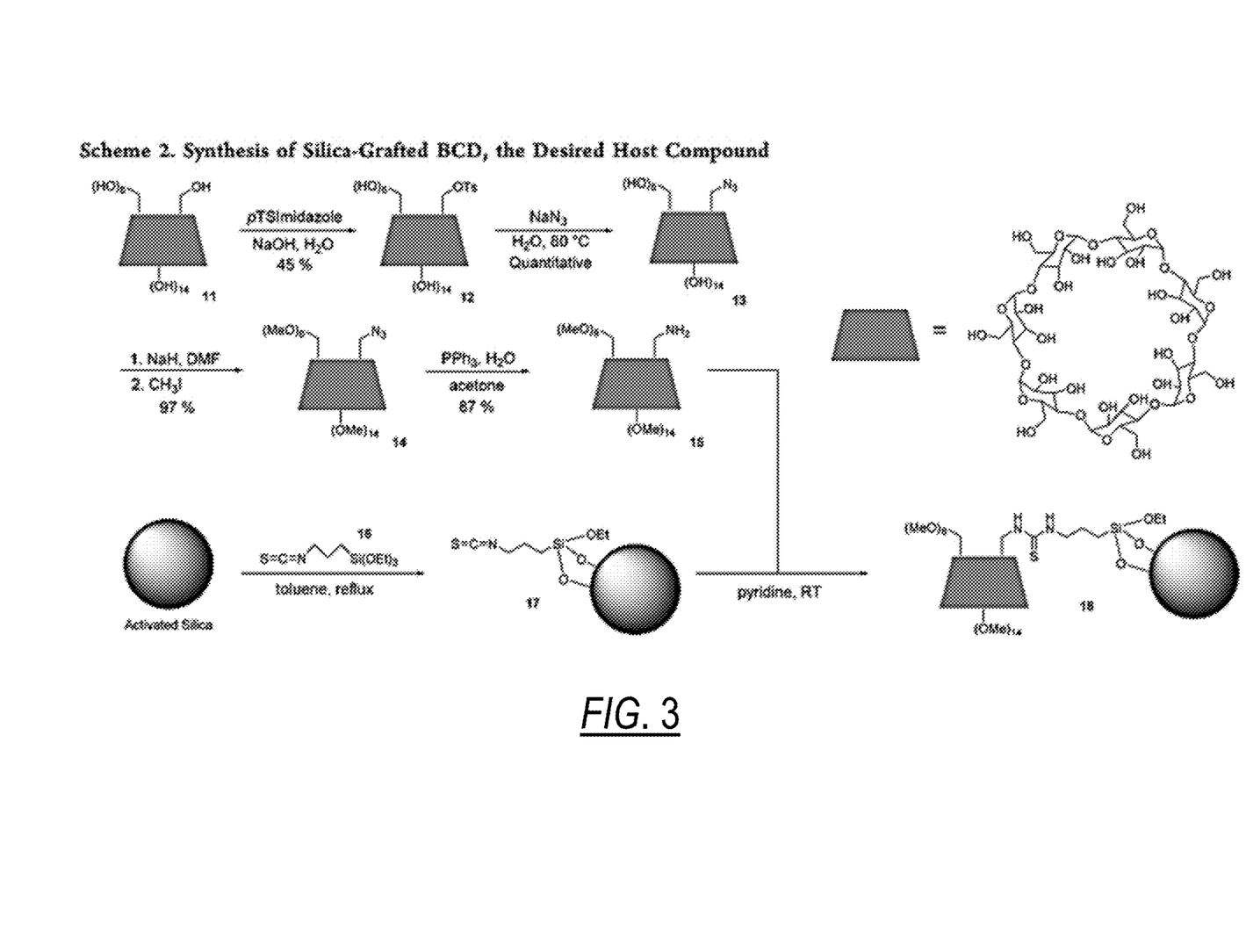
FIG. 3 is a reaction scheme illustrating an exemplary method of synthesizing Compound 18 attached to a silica substrate.

FIG. 3 outlines the method used to synthesize the host compound (Compound 18). The method began with the monotosylation of commercially available beta-cyclodextrin (BCD) using p-toluenesulfonylimidazole, which was then substituted with sodium azide to afford mono-6-azido-6-deoxy-β-cyclodextrin (Compound 13).

Reductive amination of this compound resulted in a monoamino-BCD compound that was insoluble in common metathesis solvents, requiring a different method to be adopted. To this end, Compound 14 was permethylated (PM) to yield the monoazido-PM-BCD Compound 14 in good yield after purification by column chromatography.

A Staudinger reaction with Compound 14 yielded a nnonoannino-PM-BCD (Compound 15). The treatment of Compound 15 with activated silica that had been previously functionalized with isothiocyano groups resulted in the desired host complex (Compound 18), joining cyclodextrin to the silica support via a thiourea linkage.

Additional details of these steps follow.

Synthesis of 1-(p-Toluenesulfonyl)imidazole. A 1 L, 3-necked round-bottom flask was fitted with a nitrogen inlet adapter, a pressure-equalizing addition funnel, a thermometer, and a stir bar. This flask was charged with imidazole (65 g, 954.7 mmol, 2.2 equiv.) in 250 mL dry dichloromethane and cooled to 0° C. The addition funnel was charged with a solution of p-toluenesulfonyl chloride (80 g, 419.6 mmol, 1 equiv.) in another 250 mL dry dichloromethane (0.84 M in total DCM). This solution was added dropwise at 0° C. over 1.5 hours, then warmed to room temperature and stirred for a further 2.5 hours.

The reaction was filtered through a pad of silica with 500 mL of a 1:1 hexanes:EtOAc solution. The filtrate was concentrated under reduced pressure to give an off-white solid which was dissolved in 50 mL of ethyl acetate then crashed out into 500 mL of hexanes. The desired product was collected by filtration as a white, crystalline solid. (79 g, 0.3556 mol, 85% yield).

Synthesis of Compound 12. A 1 L round-bottom flask, with no special precaution against air or moisture, was charged with 13-cyclodextrin (20 g, 17.6 mmol, 1 equiv.) and 450 mL deionized water. The mixture was heated at 60° C. with vigorous stirring until the solution became clear, then cooled to room temperature. 1-(p-Toluenesulfonyl) imidazole (15.7 g, 70.5 mmol, 4 equiv.) was ground to a fine powder by mortar and pestle before adding to the clear reaction solution all at once. The reaction was stirred for 2.5 hours at room temperature.

After the required time, the reaction mixture was charged with a solution of sodium hydroxide (9 g in 25 mL water, cooled completely to room temperature before addition) over 10 minutes via addition funnel. This reaction mixture was stirred for no more than 15 minutes after addition of base before being filtered through a glass frit to remove unreacted imidazole reagent. The filtrate was quenched by the addition of 24.1 g of ammonium chloride, which was allowed to completely dissolve before continuing.

The reaction mixture was concentrated by blowing a gentle stream of air over the flask overnight. The desired product began to precipitate almost immediately. The following morning, the reaction volume had been reduced by half and the solid product was collected by vacuum filtration and washed twice with 100 mL ice-cold water, and once with 200 mL acetone.

The collected product contained a large amount of hydrolyzed impurity which was inseparable from the desired product and therefore carried on into the next reaction where it could be easily removed. Yield is approximately 45%. Characterization data match previously-reported data.

Synthesis of Compound 13. Sodium azide (2.81 g, 43.2 mmol, 5 equiv.) was added to a solution of Compound 12 (mono-(6-p-toluenesulfonyl-6-deoxy)-13-cyclodextrin) (11.1 g, 8.64 mmol, 1 equiv.) in 108 mL (0.08 M) of deionized water in a 250 mL round-bottom flask, with no special precautions taken against air. This reaction mixture was stirred for 12 hours at 80° C.

The reaction mixture was then filtered through a fritted funnel while hot to remove hydrolyzed material from the previous reaction (insoluble in water), and the clear filtrate was added to 300 mL of acetone, causing a white solid to crash out of solution. This solid was collected by vacuum filtration and washed twice with 100 mL portions of acetone to yield 8.09 g of the desired product as a white powder. (6.97 mmol, 40% yield over 2 steps from Compound 11).

Synthesis of Compound 14. A 500 mL round-bottom flask with stir bar was charged with sodium hydride (9.50 g, 238 mmol of a 60% dispersion in mineral oil, 30 equiv.) and 156 mL dry DMF. Compound 13 (Mono-(6-azido-6-deoxy)-13-cyclodextrin) (9.22 g, 7.9 mmol, 1 equiv.) in 100 mL dry DMF was charged to the reaction vessel dropwise at 0° C. via an addition funnel. The suspension was stirred for 1 hour while warming to room temperature. The reaction was cooled back down to 0° C. and charged with methyl iodide (12.8 mL, 207 mmol, 26 equiv.) dropwise. After addition was complete, the reaction was warmed to room temperature and stirred for 16 hours.

The reaction was then quenched by the dropwise addition of methanol, and then diluted with 100 mL water. The aqueous phase was extracted with five 50 mL portions of dichloromethane. The combined organic layers were washed with brine, then dried over magnesium sulfate, filtered, and concentrated under reduced pressure. The resulting crude product was purified by column chromatography (100% DCM to 9:1 DCM:MeOH) to yield 11 g of the desired product as a yellow oil (7.64 mmol, 96% yield).

Synthesis of Compound 15. A 100 mL round-bottom flask was charged with Compound 14 mono-(6-azido-6-deoxy)-permethyl-13-cyclodextrin (11.4 g, 7.91 mmol, 1 equiv.), triphenylphosphine (2.29 g, 8.71 mmol, 1.1 equiv.), and acetone (20 mL, 0.4 M) and stirred at room temperature for 3 hours. Water (2 mL, 4 M) was added and the reaction heated to reflux for 1 hour.

The reaction was cooled to room temperature and acetone removed under reduced pressure. The resulting residue was taken into water, and the precipitated triphenylphosphine oxide was removed via filtration. The filtrate was extracted with DCM several times. The combined organic phases were dried over magnesium sulfate and concentrated under reduced pressure. The resulting crude product was purified by column chromatography (100% DCM to 9:1 DCM: MeOH) to yield 9.72 g of the desired product as an off-white oil which recrystallized upon standing (6.88 mmol, 87% yield).

Synthesis of Compound 16. A 250 mL round-bottom flask was charged with 3-aminopropyltriethoxysilane (7 mL, 30 mmol, 1 equiv.) and 20 mL anhydrous THF and cooled to 0° C. in an ice-water bath. Carbon disulfide (2.7 mL, 44.8 mmol, 1.5 equiv.) was added dropwise over 20 minutes via syringe pump, and the reaction was stirred at 0° C. for 3 hours before warming to room temperature. Dicyandiamide (3.8 g, 44.8 mmol, 1.5 equiv.) was then added in one portion, along with an additional 20 mL anhydrous THF (0.75 M total) and 3 drops of triethylamine.

This mixture was heated at 40° C. for 3 hours before the volatiles were removed in vacuo. The resulting residue was extracted with diethyl ether several times, the combined organic layers were washed twice with a small amount of water, then dried and concentrated. The resulting crude product was purified by Kügelrohr distillation (120° at 1.5 Torr) to yield 3.86 g of the desired compound as a clear yellow liquid (14.7 mmol, 49% yield).

Synthesis of Compound 17. Silica gel (70-230 mesh, 60 Å pore size, 550 m$^2$/g) was activated by stirring in 50:50 HNO$_3$ (70%):H2O at reflux for 24 hours. The newly activated silica was collected by vacuum filtration and washed several times with water, then methanol. The silica was then collected and dried in a vacuum oven at 100° C. overnight, and stored in an air-free environment prior to use.

Activated silica (5 g) was dispersed in toluene (50 mL) with vigorous stirring for 5 minutes before being charged with Compound 16 (3 grams, 11.4 mmol). This mixture was heated at reflux for 24 hours with gentle stirring before being cooled to room temperature. The cooled mixture was collected by filtration and washed several times with toluene before being dried in a vacuum oven at 60° C. for 16 hours. This product was carried on immediately without further purification.

Synthesis of Compound 18. Isothiocyanate-grafted silica (17, 500 mg) was added to a solution of Compound 15 (1 g) and pyridine (minimum to dissolve, ~2 mL). This suspension was stirred at room temperature for 48 hours.

The silica compound was collected by vacuum filtration and washed several times with water, then methanol, then finally with diethyl ether. The recovered host compound was dried in a vacuum oven at 60° C. for 16 hours, and then stored in a moisture-free environment before being subjected to FT-IR and TGA characterization methods, as detailed in the manuscript.

Figure 4:
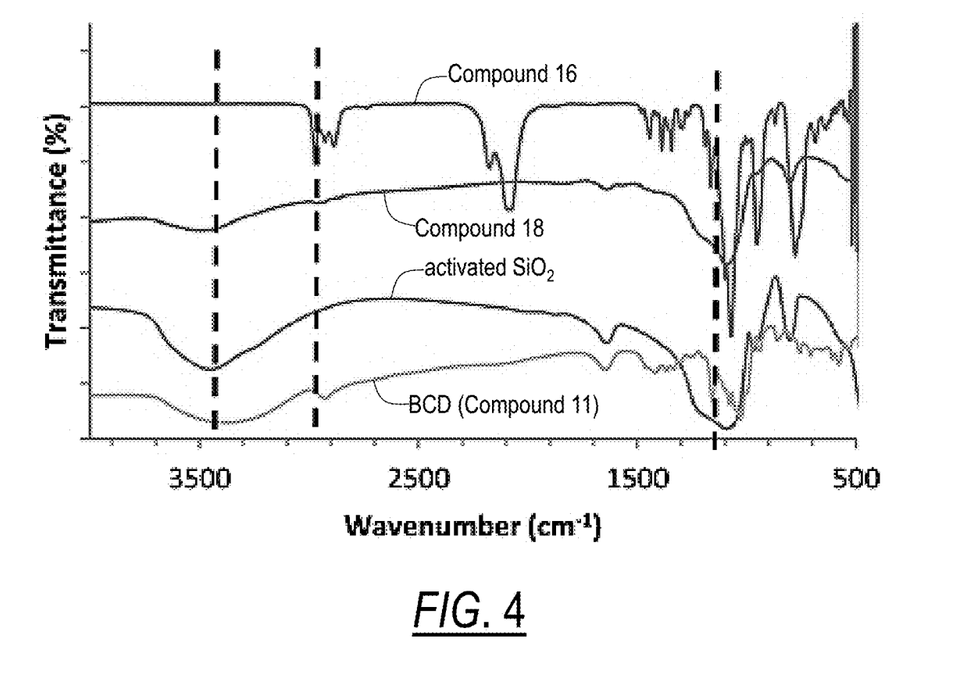
FIG. 4 is a set of FT-IR spectra for the species indicated.

Characterization of Compound 18. Referring to FIG. 4, Fourier transform infrared (FT-IR) data confirmed Compound 18 was created. The broad peaks at approximately 3450 cm$^{-1}$ are O—H stretching vibrations present in either unaltered BCD or on the surface of the silica gel. The IR spectra of Compounds 14 and 15 show no such peak, indicating that the observed O—H stretching peaks in Compound 18 are due to those present on the surface of the silica.

The sharper peaks at 2950 cm$^{-1}$ are the C—H stretching frequencies of PM-BCD. Additionally, the strong and broad peaks at approximately 1075 cm$^{-1}$ in the spectra of Compound 18 and silica are assigned to Si—O stretching vibrations.

Figure 5:
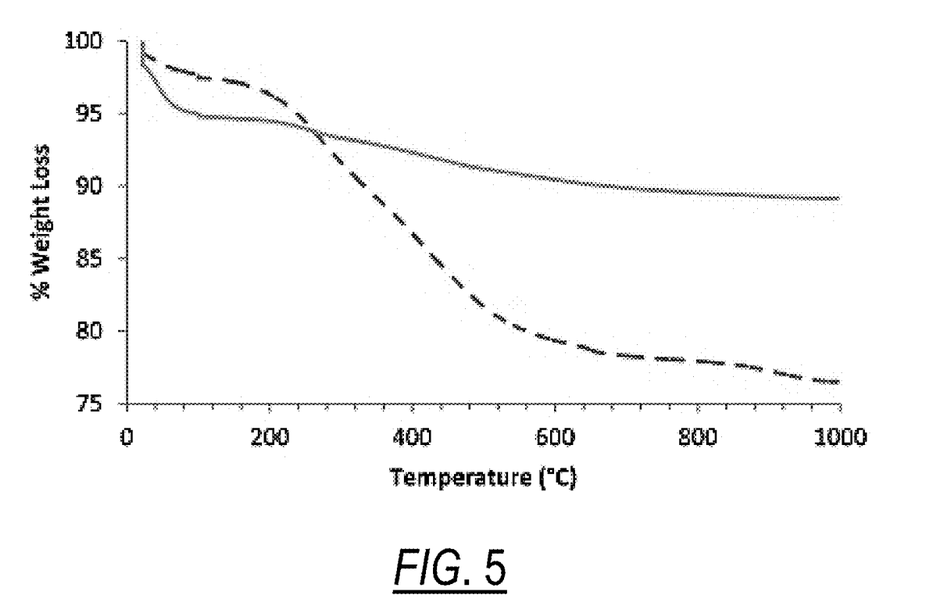
FIG. 5 is a set of TGA curves for silica (solid line) and Compound 18 (dashed line).

Referring to FIG. 5, thermogravimetric analysis (TGA) was applied to Compound 18 to quantify the degree of functionalization of the surface of the silica gel with PM-BCD. Silica gel itself showed a loss of about 5% before 200° C., likely due to the presence of adsorbed water on the surface of the silica. A further 6% of weight loss is attributed to the dehydration of surface hydroxyl groups on silica.

Compound 18 showed water loss at about 3.4% before dropping in weight between 220 and 600° C. This drop in weight is due to the thermal decomposition of PM-BCD moieties. This provides direct evidence of the grafting of PM-BCD units onto the silica gel, with a concentration of 1.43×10$^{-4}$ mmol PM-BCD mg$^{-1}$.

Recovery of Compound 4 Before used in a Reaction

Figure 6:
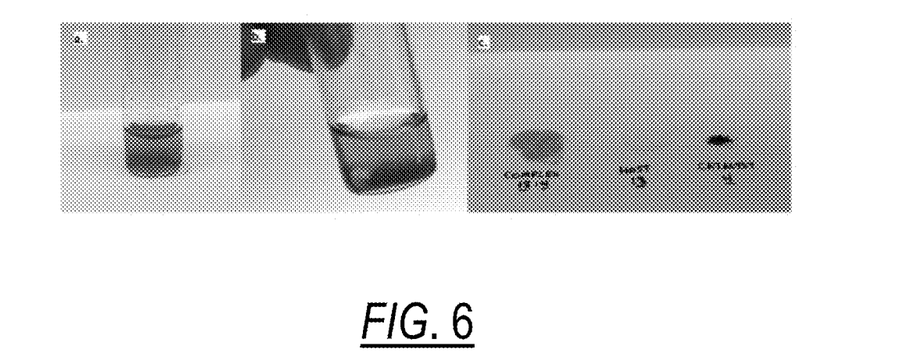
FIG. 6 is a set of photographs of a mixture of Compounds 4 and 18 in 1 mL of toluene (left panel); the same mixture after the host-guest compound has formed and precipitated (middle panel); and a visual comparison of the host-guest compound, the host compound, and the catalyst (right panel).

Referring to FIG. 6, the homogeneous catalyst (Compound 4) can be removed from solution via host-guest complexation with Compound 18.

A vial containing 1 mg of Compound 4 in 1 mL of dry and degassed toluene was stirred with 2 equiv. of host Compound 18 attached to the silica substrate, based on the surface coverage of the PM-BCD calculated above. After 15 min of stirring, the contents were allowed to settle. The silica-supported host-guest complex settled out as a dark solid, leaving the previously golden-brown solution a much lighter yellow. Filtering this solution through a filter paper yielded a dark solid, distinct from both the white host compound and the dark yellow-green catalyst, confirming that Compound 4 forms a host-guest complex with silica-attached Compound 18.

Catalyzed Reactions

Adding the azobenzene moiety did not significantly affect the catalyst's activity. Two benchmark ring-closing metathesis (RCM) substrates were chosen. They are Compound 19 and Compound 21 in FIG. 6. The efficiency of Compound 4 was compared to that of the Hoveyda-Grubbs' second-generation catalyst (Compound 3).

The RCM reactions were carried out in dichloromethane (DCM) at 40° C. under typical metathesis concentrations, and the reactions were monitored by gas chromatography (GC) using mesitylene as an internal standard. In the reaction of diethyl diallylmalonate (Compound 19), Compound 4 performed comparably to Compound 3, reaching >90% conversion in 30 min.

The evaluation of the catalytic efficiency of Compound 4 was extended to the more hindered diene (Compound 21). The reaction was slower for both catalysts. Compound 3 required 30 min to achieve greater than 90% conversion, with full conversion taking 3 hours. Compound 4 achieved 80% conversion after 30 min and 86% conversion after 5 hours.

Even more hindered substrates, such as diethyl di(2-methylallyl)malonate (Compound 23), showed a very low conversion for both catalysts even after 5 h, indicating that Compound 4 compares well with other commercially available metathesis catalysts.

Recovery of Compound 4 after Catalyzing a Reaction

Figure 7:
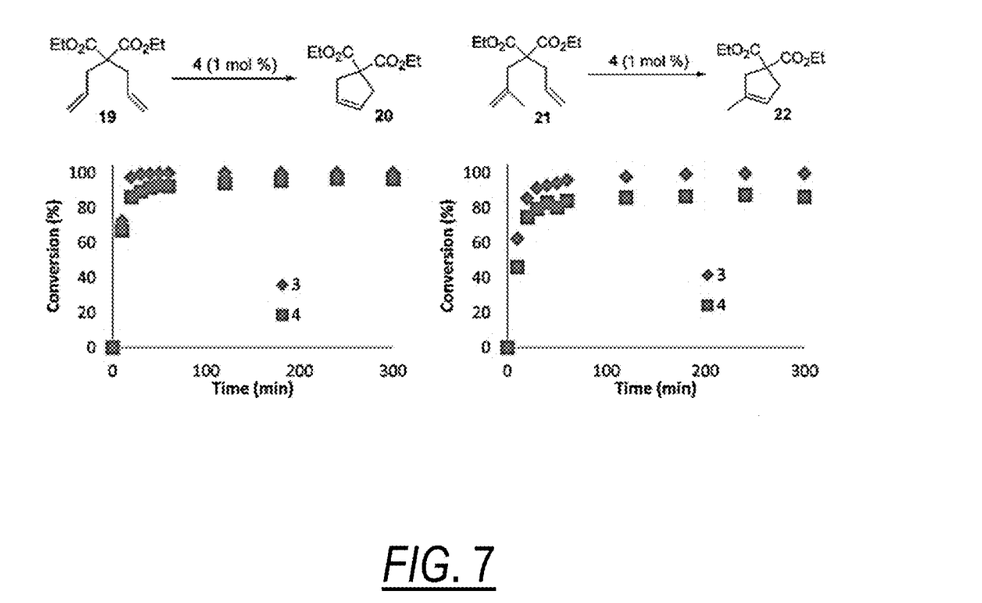
FIG. 7 is a set of graphs of the conversion percentage vs. time for the ring closing metathesis reaction shown above each graph comparing using Compound 4 and Compound 3 as the catalyst.
Figure 8:
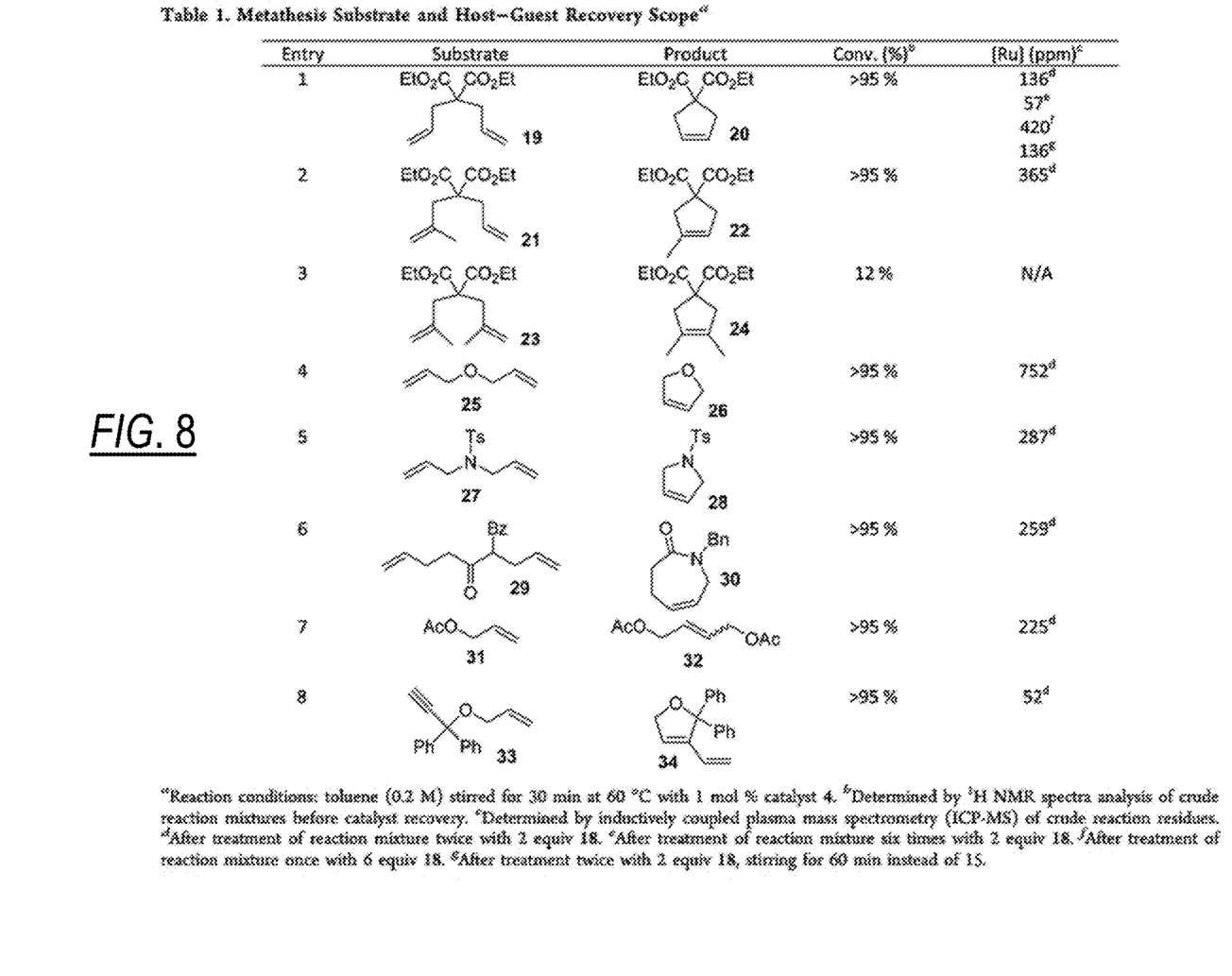
FIG. 8 is a table showing the metathesis substrates tested, the product formed, the conversion percentage, and the amount of Ru recovered using Compound 4 as the catalyst.

The catalyst (Compound 4) is recoverable from a chemical reaction solution after catalyzing a reaction. The metathesis substrates shown in FIG. 7 were screened. The reactions were run under optimized conditions, using 1 mol % of Compound 4 as the catalyst, with dry and degassed toluene as a solvent, at 60° C. for 30 min before analysis of the crude reaction mixture by $^1$H NMR spectroscopy. The results are summarized in FIG. 7.

Catalyst recovery was examined by varying the amount of host (Compound 18) and number of recovery cycles performed. After the ring closing metathesis (RCM) reaction of Compound 19, Compound 18 was added in one portion and stirred at room temperature for 15 min. During this time, the reaction vessel was irradiated with visible light for 30 seconds with a 500 W halogen work lamp to ensure that trans isomer form of the azobenzene functional group on Compound 4 was present in solution. This caused the host-guest compound to form.

The contents of the reaction vessel were filtered with the host-guest complex (Compound 18:Compound 4) separated from the solution onto a filter paper. The residual ruthenium content of the reaction solution was evaluated by ICP-MS analysis and displayed in parts per million, defined as micrograms of ruthenium per gram of product.

Treating the crude reaction mixture twice using 2 equiv of Compound 18 (2×2 equiv) was more effective than treating it only once with 6 equiv of Compound 18 (1×6 equiv), with residual ruthenium contents of 136 and 420 ppm, respectively. Extensive treatment with Compound 18, a 6×2 equiv method, resulted in only 57 ppm remaining ruthenium, although this additional recovery may not justify the amount of time and the host compound consumed in the process.

It was found that increasing the stirring time from 15 to 60 min upon addition of 18 (2×2 equiv) did not increase the amount of ruthenium recovered from solution, with both experiments yielding 136 ppm ruthenium, indicating that complexation occurs rapidly.

After these initial experiments were performed with Compound 19, the other substrates and a blank sample were treated with 2×2 equiv host compound 18. The results are displayed in FIG. 7.

The amount of residual ruthenium after recovery by the host compound varied from 752 ppm to as low as 52 ppm, although all examples were greatly reduced from the starting ruthenium concentration, calculated to be 4772 ppm. The blank sample showed essentially 0 ppm ruthenium. These results were gained by a vacuum filtration of the crude reaction mixture. Centrifugation and other advanced separation techniques did not improve the result.

This disclosure describes certain exemplary embodiments, but not all possible embodiments of the composition and methods. Where a particular feature is disclosed in the context of a particular embodiment, that feature can also be used, to the extent possible, in combination with and/or in the context of other embodiments. The composition and methods may be embodied in many different forms. The claims should not be construed as being limited only to the embodiments described here.

That which is claimed is:

1. A method of performing a catalyzed chemical reaction, the method comprising:
   catalyzing a chemical reaction in a solution using an azobenzene-modified Grubbs homogeneous catalyst;
   adding a host compound to the solution, the host compound binding a first isomer of the catalyst to form a host-guest compound including the host compound and first isomer of the catalyst, the host compound being a cyclodextrin;
   isolating the host-guest compound from the solution; and
   releasing the catalyst from the host-guest compound by converting the first isomer of the catalyst to a second isomer of the catalyst.

2. The method of claim 1, wherein first isomer is a cis or trans isomer and the second isomer is the other of a cis or trans isomer.

3. The method of claim 1, wherein the homogeneous catalyst includes a transition metal and an N-heterocyclic carbene moiety bonded to an azobenzene moiety.

4. The method of claim 1, wherein the cyclodextrin attached to a surface of a substrate.

5. The method of claim 1, wherein the chemical reaction is an olefin metathesis reaction.

6. The method of claim 1, wherein converting the first isomer of the catalyst to a second isomer of the catalyst includes applying electromagnetic radiation.

7. The method of claim 1, wherein:
   the catalyst is converted from the first isomer to the second isomer by applying electromagnetic radiation that causes the azobenzene functional group to undergo an isomerization change.

8. A composition comprising a homogeneous catalyst including a transition metal complex having an N-heterocyclic carbene ligand with an azobenzene functional group thereon, the azobenzene functional group being effective to undergo cis-trans isomerization;
   the composition having the formula where R indicates the position of the azobenzene functional group.

9. The composition of claim 8, further comprising a cyclodextrin moiety bound to the azobenzene functional group.

10. The composition of claim 9, further comprising a silica substrate attached to the cyclodextrin moiety.

11. The method of claim 1, wherein the homogeneous catalysts has the formula

12. The composition of claim 8, wherein the homogeneous catalysts has the formula

* * * * *